United States Patent [19]
Oppenheimer et al.

[11] Patent Number: 5,916,152
[45] Date of Patent: Jun. 29, 1999

[54] LUNG PERMEABILITY ANALYSIS

[75] Inventors: Luis Oppenheimer; Henry H. Mantsch; Michael G. Sowa; Jing Wang, all of Winnipeg, Canada

[73] Assignees: Coretech Medical Technologies Corp.; National Research Council of Canada, both of Winnipeg, Canada

[21] Appl. No.: 08/857,012

[22] Filed: May 15, 1997

[51] Int. Cl.$^6$ ............................................. A61B 5/00
[52] U.S. Cl. ................................................. 600/310
[58] Field of Search .......................... 600/310, 314, 600/316, 322, 342, 473, 476; 250/302, 339.07

[56] References Cited

PUBLICATIONS

Heyn, "The infrared absorption spectrum of dextran and its bound water," Biopolymers, pp. 475–506, Mar. 1974.

McNamee, "Restricted dextran transport in the sheep lung lymph preparation," Journal of Applied Physiology, pp. 585–590, Mar. 1982.

Pietra, et al., "Permeability of pulmonary endothelium to neutral and charged macromolecules," Annals of the New York Academy of Sciences, pp. 241–247, 1982.

H.M. Heise, R. Marbach, Th. Koschinsky, and F.A. Gries, Multicomponent Assay for Blood Substrates in Human Plasma by Mid–Infrared Spectroscopy and its Evaluation for Clinical Analysis, *Applied Spectroscopy*, 48(1): 85–95 (1994).

R. Anthony Shaw et al, Quantitation of Protein, Creatinine, and Urea in Urine by Near–Infrared Spectroscopy, *Clinical Biochemistry*, 29:11–19 (1996).

H.H. Eysel, Henry H. Mantsch and Michael Jackson, Infrared spectra of joint fluids, *Intern. Society of Optical Eng.*, 2089:136–137 (1993).

L. Oppenheimer and D. Huebert, Near–infrared spectrophotometric device to measure fluid exchange in blood–perfused organs, *Journal of Applied Physiology*, 74(5): 2205–2213 (1993).

L. Oppenheimer et al, Colorimetric device for measurement of transvascular fluid flux in blood–perfused organs, *Journal of Applied Physiology*, 62(1):364–372 (1987).

P.N. Lanken et al, Passage of uncharged dextrans from blood to lung lymph in awake sheep, *Journal of Applied Physiology*, 59(2):580–591 (1985).

*Primary Examiner*—Max Hindenburg
*Assistant Examiner*—Eric F. Winakur
*Attorney, Agent, or Firm*—Timothy R. Kroboth

[57] ABSTRACT

A spectrophotometric analytical method for lung permeability is described. An exogenous polydispersed macromolecule is administered, and fluid of the patient is evaluated using infrared spectroscopy.

11 Claims, 10 Drawing Sheets

A: PLASMA WITH PENTASTARCH
B: PLASMA WITHOUT PENTASTARCH
C: URINE WITH PENTASTARCH
D: URINE WITHOUT PENTASTARCH fig. 7.

TOP: HIGH GLUCOSE CONCENTRATION
BOTTOM: LOW GLUCOSE CONCENTRATION

LUNG PERMEABILITY ANALYSIS

The present invention relates to the infrared analysis of lung microvascular permeability.

High and low molecular weight hydroxyethyl starches (HES) are commonly used as colloid plasma volume expanders during surgery and as an adjunct to treatment of shock. Similarly, dextran has been used as a colloid plasma volume expander. More recently, HES has been used in septic patients with acute lung injury with the goal of maintaining plasma colloid osmotic pressure in favour of intravascular fluid retention. However, the effectiveness of colloid administration in patients with acute lung injury remains controversial.

Methods for determining lung microvascular permeability typically rely on the use of radioactive isotopes or dye-labelled tracers. However, the use of labelled tracers raises safety questions and associated ethical issues.

By the present invention, lung alveolo-capillary permeability is beneficially evaluated without use of labelled tracers. Furthermore, significant data may be obtained with minimal invasiveness. Also, rapid evaluation is possible.

In accordance with the present invention, a patient is beneficially administered a suitable exogenous macromolecular colloid recognizable by infrared analysis. An appropriate dosage is typically administered intravenously. Thereafter, bronchial-alveolar fluid of the patient is analyzed by infrared analysis, for the exogenous macromolecule.

Infrared analysis of the level of the exogenous macromolecule in the plasma advantageously provides for a determination of the bronchial/plasma ratio of the exogenous macromolecule. For pharmacokinetic information on the macromolecule clearance, urine levels may be collected for analysis.

The methodology of the present invention provides an exogenous marker useful for assessing the degree of lung injury and for monitoring the progress of lung injury disease, as well as for monitoring plasma colloid osmotic pressure maintenance in cases of acute lung injury. The methodology may be used in particular in connection with adult respiratory distress syndrome (ARDS), the result of acute lung injury that leads to noncardiogenic pulmonary edema through an increase in pulmonary capillary permeability. Diagnosis of ARDS is provided for. Beneficially, the methodology is suited for routine use in a critical care environment.

In the drawing and in the detailed description of the invention that follows, there are shown and essentially described only preferred embodiments of this invention. As will be realized, this invention is capable of other and different embodiments, and its several details are capable of modification in various respects, all without departing from the invention. Accordingly, the drawing and the detailed description are to be regarded as illustrative in nature, and not as restrictive.

BRIEF DESCRIPTION OF THE DRAWING

Reference is now made to the accompanying drawing, which forms a part of the specification of the present invention.

DETAILED DESCRIPTION OF THE INVENTION

In accordance with the present invention, it has been discovered that a defining characteristic of a useful exogenous macromolecule is a spectroscopic IR signature distinguishable from endogenous components of bronchial fluid or plasma. By this approach, a labelled tracer is made unnecessary. In particular, it has been found that a strong IR absorption in the range of about 900 to 1200 $cm^{-1}$, sometimes referred to as the sugar absorption region, is distinctive using mid-infrared spectroscopy, and also that an IR absorption in the range of about 4350 to 4500 $cm^{-1}$ is distinctive using near-infrared spectroscopy. In this regard, it has been found that a useful macromolecular marker may advantageously include a sugar moiety, in particular a pyranosyl moiety. Beneficially, this moiety is found in known artificial colloids.

It will, of course, be understood that a distinctive IR signature other than in the foregoing regions, can be used in accordance with the present invention. For instance, near-infrared spectroscopy (about 4000 or to 16000 $cm^{-1}$, or about 2500 to 600 nm) may include other regions useful in certain applications.

In accordance with the present invention, artificial polydispersed colloids are especially useful, exogenous macromolecules. A beneficial attribute of polydispersed colloids is a broad molecular weight distribution. Typically, only the small sized macromolecules, if any, will pass or escape from the intravascular space into the interstitium of the lung, whereas larger sized macromolecules are confined to the intravascular space, in the case of normal lung microvascular permeability. However, in pathological conditions associated with increased lung alveolo-capillary permeability, some macromolecular sizes will pass into the lung interstitium and from there into the alveolar space, depending upon the degree of the permeability-enhancing lesion, and the upper range of the macromolecular sizes. Beneficially, administration of a spectrum of different sized macromolecules presents a membrane with a gradation of sizes, and permits evaluating the degree of a lesion or lesions.

Similarly, other distinguishable, exogenous macromolecules characterized by a useful range of molecular weights, may be used in the present invention. These macromolecules may be characterized by a distinctive IR signature in a region other than the regions specifically pointed out earlier.

By comparison, colloids such as albumin lack an advantageous molecular weight distribution, and thus would not be considered "polydispersed" for purposes of the present invention. In addition, albumin is an endogenous macromolecule and would therefore be labelled for use as a tracer. As mentioned, a benefit of the present invention is that a labelled tracer is unnecessary.

Accordingly, polydispersed colloids are advantageous as a tracer of abnormal lung permeability, in accordance with the methodology of the present invention. Illustrative polydispersed colloids include high molecular weight, hydroxyethyl starches such as HES 450/0.7 (average molecular weight/degree of substitution), low molecular weight, hydroxyethyl starches such as HES 125/0.7, 150/0.7, 200/0.5, and 264/0.45, and dextrans such as dextran 40, dextran 50, dextran 60 and dextran 70. Each of these specifically mentioned colloids has a molecular weight distribution that beneficially presents lung alveolo-capillary membranes with a gradation of sizes, and permits assessing the degree of a lesion or lesions. A substantially uniform distribution as in the case of hydroxyethyl starches such as HES 450/0.7 and HES 200/0.5, can be of further advantage; by comparison, bell-shaped curves characterize the distribution of dextrans such as dextran 40 and dextran 70.

Hetastarch is a high molecular weight, hydroxyethyl starch, which is formulated as 6 gm hetastarch/100 ml. The average molecular weight is approximately 450,000, with 90% of the polymer units falling within the range of 10,000 to 1,000,000. The degree of substitution is 0.7, which means that hetastarch has 7 hydroxyethyl groups for every 10 glucose units. Hetastarch is derived from a waxy starch composed almost entirely of amylopectin.

A related, useful low molecular weight, hydroxyethyl starch is pentastarch, which is sold in a formulation of 10 g pentastarch/100 ml. Pentastarch is a low molecular weight, low molar substitution, hydroxyethyl starch having an average molecular weight of 200,000 to 300,000, and a degree of substitution of 0.40 to 0.50, which means that pentastarch has approximately 45 hydroxyethyl groups for every 100 glucose units. Pentastarch is likewise derived from a waxy starch composed almost entirely of amylopectin.

Previous workers have found that pentastarch is eliminated much faster than hetastarch in studies of healthy volunteers, and that the amount of hydroxyethylation is more important than molecular weight in determining the rate of elimination of HES. Thus, for example, HES 264/0.45 is reported to have a faster rate of urinary excretion than HES 150/0.7. The hydroxyethyl group is not cleaved, but remains intact and attached to glucose units when excreted.

Dextran 70 is that fraction of dextran having an average molecular weight of 70,000. Approximately 60% of dextran 70 molecules are above the upper renal filtration threshold. Similarly, dextran 40 is that fraction of dextran having an average molecular weight of 40,000.

Since the renal threshold for dextrans is about 55,000 daltons, dextran fractions with molecular weight less than 55,000 are freely eliminated by renal excretion. More specifically, the half-life in healthy volunteers is about 30 minutes for the fraction ranging from about 28,000 to 36,000 daltons, about 7.5 hours for the fraction ranging from about 44,000 to 55,000 daltons, and much greater than 12 hours for more than 55,000 daltons. Thus, the elimination rates of dextrans are determined by molecular weight.

As may therefore also be understood, the distribution of polydispersed colloid fractions in plasma will shift to a higher molecular weight with time, in particular typically within about several hours or less of administration. This shift results from rapid renal excretion of the lower molecular weight fractions, and much slower elimination of the higher molecular weight fractions. Enzymatic hydrolysis producing lower molecular weight macromolecules from higher molecular weight macromolecules, will, of course, affect the shift.

Figure 1:
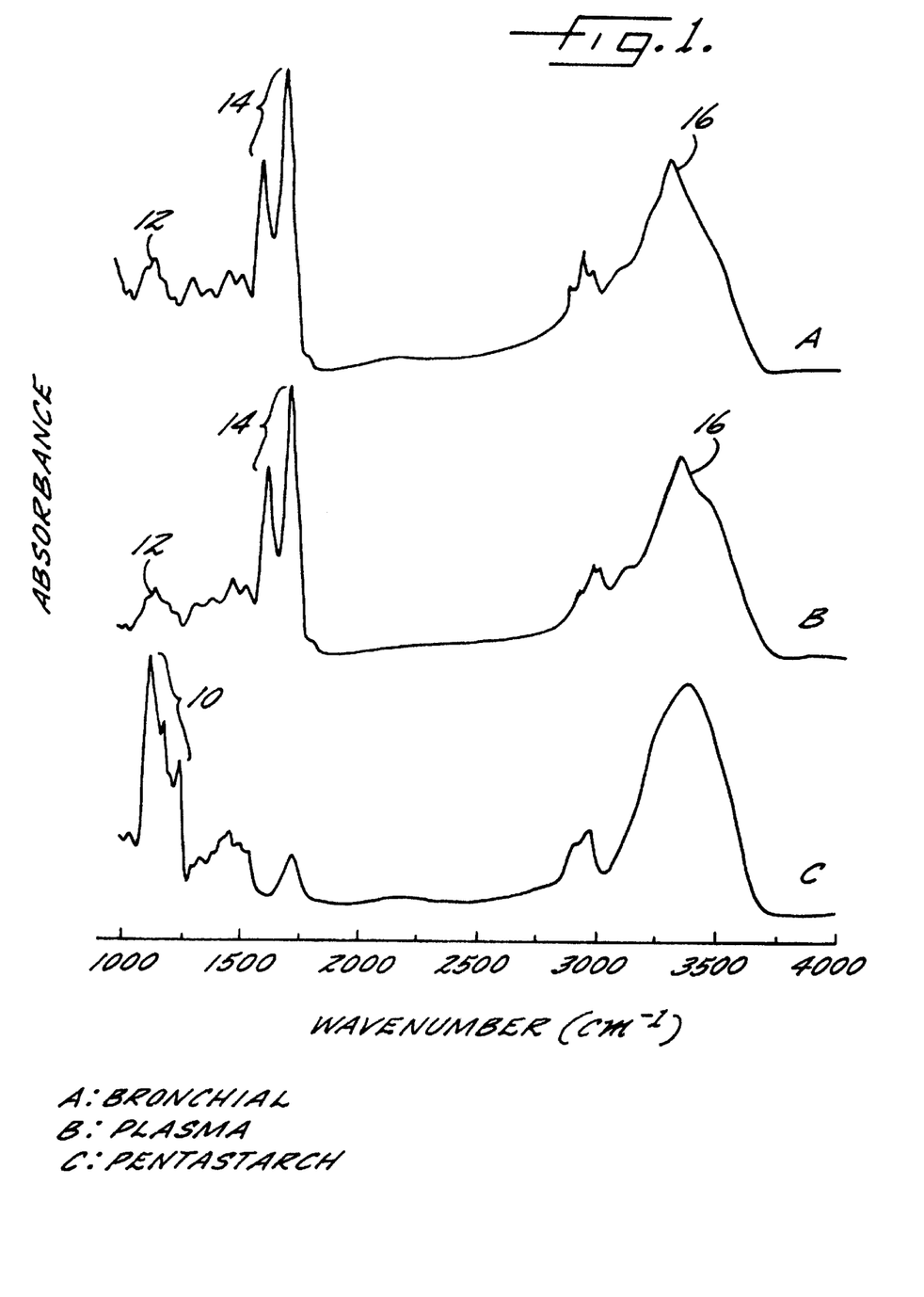
FIGS. 1 to 3 are mid-infrared spectra.

Shown in FIG. 1 is the mid-infrared spectrum of pentastarch (line C). Line C is obtained by IR spectroscopy of a film dried from 10% pentastarch in isotonic saline. Also shown in FIG. 1 are comparison spectra of bronchial fluid (line A) and plasma (line B). Line A is obtained for a film dried from a bronchial washing, and line B is obtained for a film dried from a plasma sample.

Line C shows particularly distinct features in the region between 980 to 1190 $cm^{-1}$, and is characterized by strong absorption (indicated by the numeral 10), compared to weak absorption (indicated by the numeral 12) of the bronchial fluid and plasma in this region. Protein components are thought to primarily account for the strong absorptions (indicated by the numerals 14, 16) of bronchial fluid and plasma.

Figure 2:
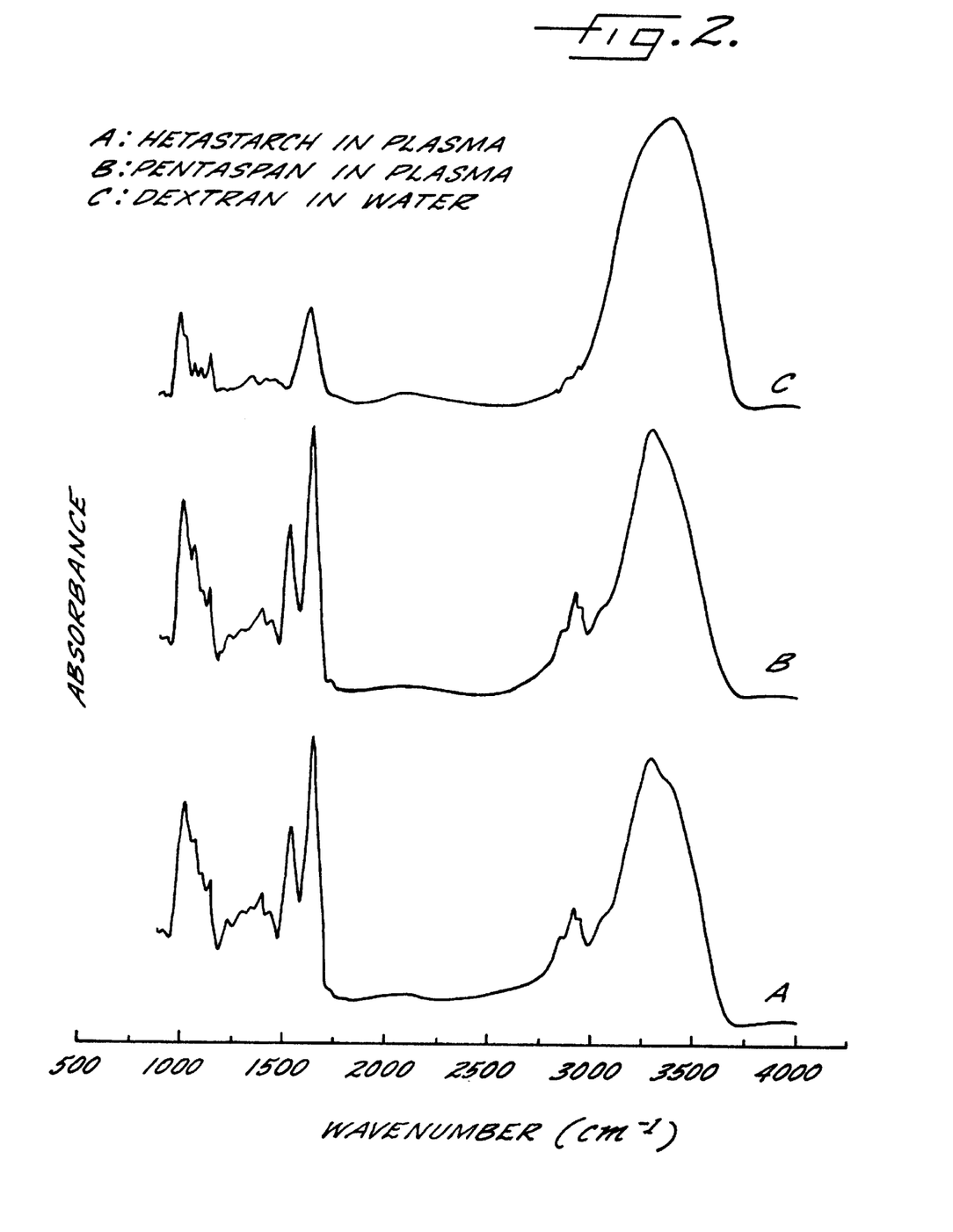

Shown in FIG. 2 are IR spectra for hetastarch in plasma (line A), pentastarch in plasma (line B), and dextran 70 in water (line C). As may be noted, each of these spectra shows the characteristic sugar region absorption.

Useful exogenous macromolecules are further beneficially characterized by acceptance in terms of clinical safety. Thus, as may be understood, it is advantageous that clinically accepted macromolecules for patient administration include polydispersed colloids.

In accordance with the invention, a suitable dose of a useful macromolecule is administered to a patient, typically intravenously. The dose should be sufficient to obtain a plasma level adequate for IR spectroscopic recognition. As may be understood, the dose will vary depending upon other factors including the weight of the patient and clinical considerations. A typical dose may be in the range of about 100 to 1000 ml in the case of a hydroxyethyl starch. As indicated, a suitable dose may be dictated by other clinical objectives such as use as a colloid plasma volume expander, and could be greater or less than the given range.

After a sufficient period of time to allow for leakage into the alveolar space in the case of abnormal lung permeability, bronchial fluid of the patient is analyzed. Generally speaking, this waiting period may be relatively short. Typically, there will be no significant advantage in a waiting period that is more than about one hour from the time of administration of the macromolecule, although circumstances vary.

Bronchial fluid samples may be collected for analysis, or bronchial fluid may be analyzed in situ. For this purpose, broncho-alveolar-lavage or bronchial washings may be used, or bronchial fluid may be analyzed without removal by use of suitable fiber optic instrumentation inserted into the lung. Near-infrared analysis is particularly suitable for fiber optic evaluation of bronchial fluid. In accordance with the invention, other useful biofluid samples are suitably collected from the patient using common techniques, with the timing for collection typically being substantially simultaneously with the bronchial fluid in the case of plasma samples.

Broncho-alveolar-lavage is a common technique of obtaining bronchial fluid for analysis, usually cytology, biochemistry and culture. When using this technique, a specialist inserts a bronchoscope, and irrigates and samples the fluid.

Figure 6:
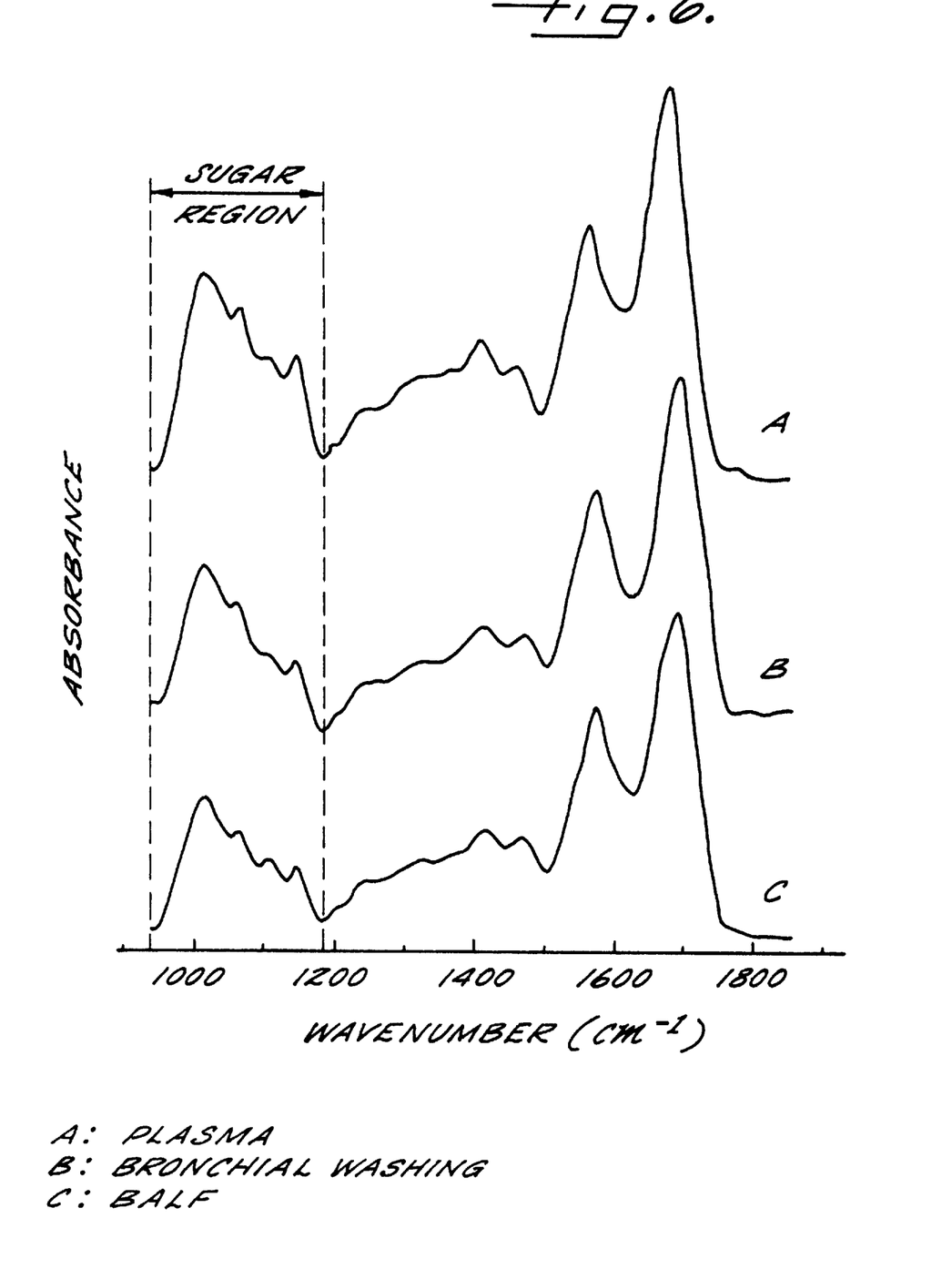

In accordance with the invention, it has been found convenient, as shown in FIG. 6, to collect bronchial fluid as bronchial washings. Because of less invasiveness, this technique is preferable to broncho-alveolar-lavage. Also, nurses frequently instill fluid to clear secretions from endotracheal tubes and airways on intubated patients. Because this is typically done routinely, bronchial washings are available, and are thus useful for screening in accordance with the methodology of the present invention. When bronchial washings from routine pulmonary toilet are used, the period of time that elapses between administration of the macromolecule and sampling the bronchial fluid, may be determined by this schedule.

Frequently, as indicated, a critical care patient will be intubated and on positive pressure ventilation. In such patients, collection as bronchial washings may be achieved by advancing a suction catheter through the endotracheal tube until a slight resistance is felt, generally a distance of 35 to 40 cm. When no fluid comes back spontaneously, a sufficient volume of a suitable diluent or carrier such as normal saline, is beneficially flushed down the catheter to provide several milliliters of a bronchial washing. However, when fluid does come back spontaneously, it is not necessary to add the diluent or carrier. After several respiratory cycles, negative pressure is used for aspiration and then the catheter is withdrawn. Aspirated fluid is collected, the usual yield being about 3 to 4 ml, although more or less may be obtained depending upon the collection procedure.

In accordance with the invention, a biofluid sample is analyzed using IR spectroscopy. Prior to analysis, it is generally beneficial for mid-infrared analysis, to homogenize bronchial fluid samples sufficiently for sample uniformity. Conveniently, homogenization may be for about 2–3 minutes at a speed of about 100 rpm. Analysis is conveniently accomplished by use of conventional IR spectrometric instrumentation.

In a useful technique, a sample may be diluted with distilled water to adjust sample concentration to the optimal spectroscopic range, and thereafter for mid-infrared analysis, a small volume of the diluted sample may be placed on a carrier suitable for IR spectroscopy such as 25×2 mm $CaF_2$ window, and dried down in a vacuum desiccator to form a film on the carrier. Then, the film sample is analyzed.

Figure 3:
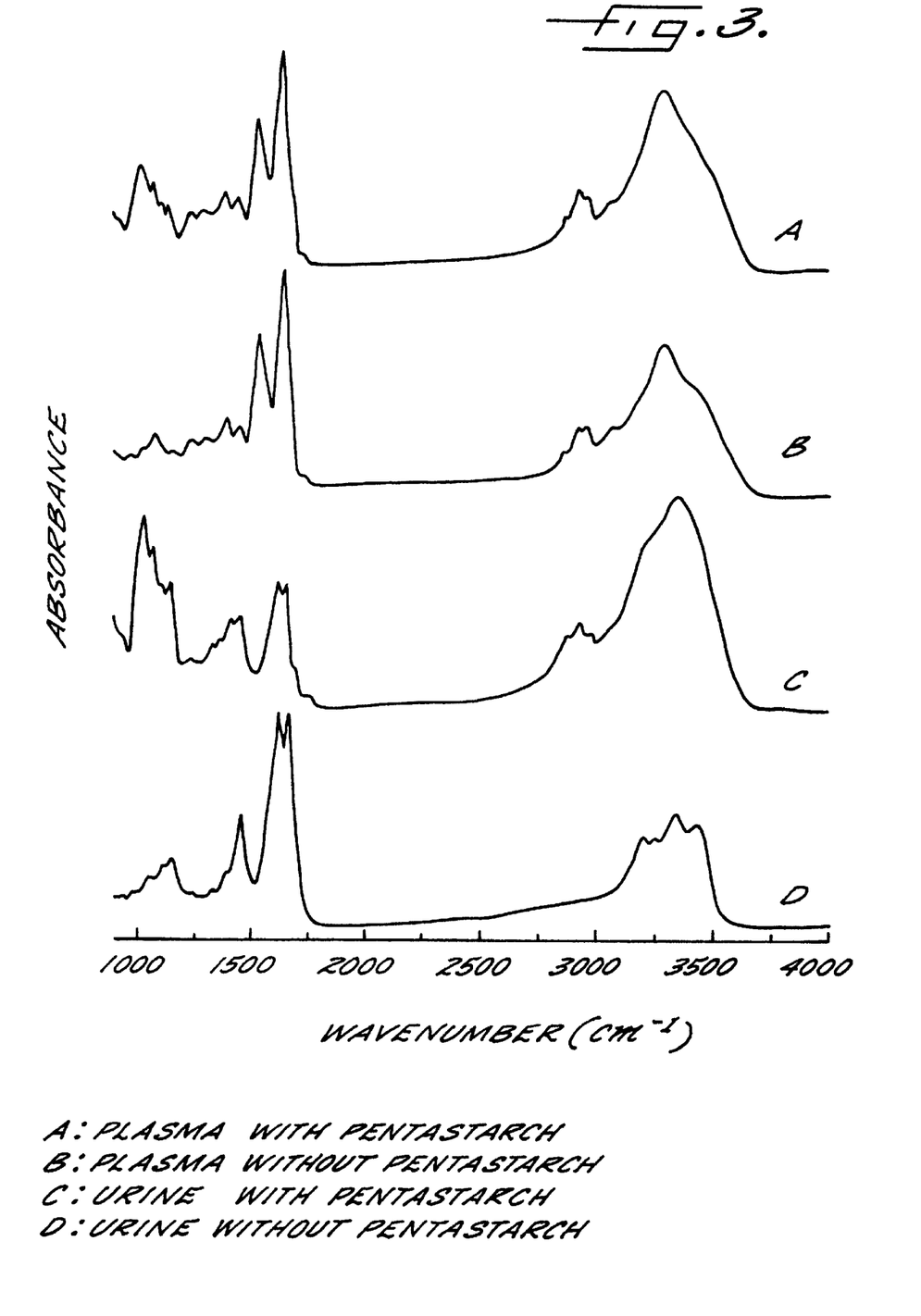

FIG. 3 displays the IR spectrum of plasma acquired before (line B) and after (line A) infusion of 500 ml of pentastarch, and a reference spectrum of urine acquired before (line D) and approximately 17 hours after (line C) the pentastarch infusion. Hydrolysis by serum alpha-amylases converts the pentastarch into subunits small enough to be filtered and eliminated by the kidney. Strong absorption bands characteristic of pentastarch and hydrolyzed pentastarch subunits (980 to 1190 $cm^{-1}$), are discernible in lines A and C of FIG. 3.

Because the intensity of the IR absorption is proportional to exogenous macromolecule concentration in the biofluid, quantitation is possible, for instance, by integrating the area of the sugar absorption region between 980 and 1190 $cm^{-1}$. As appropriate, correction should be made for sample dilution.

Figure 4:
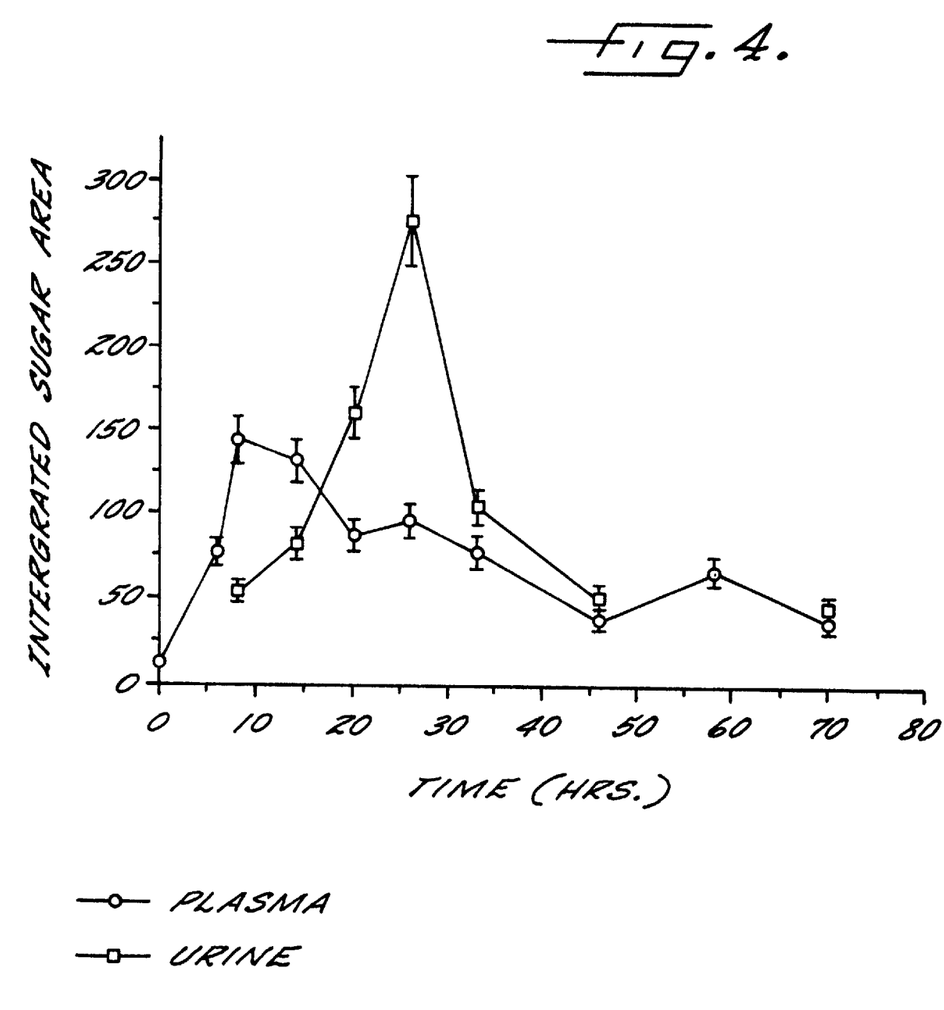
FIG. 4 graphically correlates concentration of a useful exogenous macromolecule in accordance with the present invention, in the plasma and urine, over time.

As shown in FIG. 4, the methodology of the present invention may also be used to monitor levels of a macromolecule in accordance with the present invention, in plasma and urine, thus providing pharmacokinetic information on the macromolecule clearance. More precisely, FIG. 4 correlates pentastarch concentration in the plasma and urine, as determined using the integrated 980 to 1190 $cm^{-1}$ band area, over a period of about eighty hours, for a patient receiving three pentastarch infusions: the first being 600 ml and being given at to, the second being 1000 ml and being given an hour later, and the third being 500 ml and being given six hours after the second infusion. In this particular case, the highest urinary concentration of the pentastarch hydrolysate is found to occur about seventeen hours after the maximum intravascular concentration.

Figure 5:
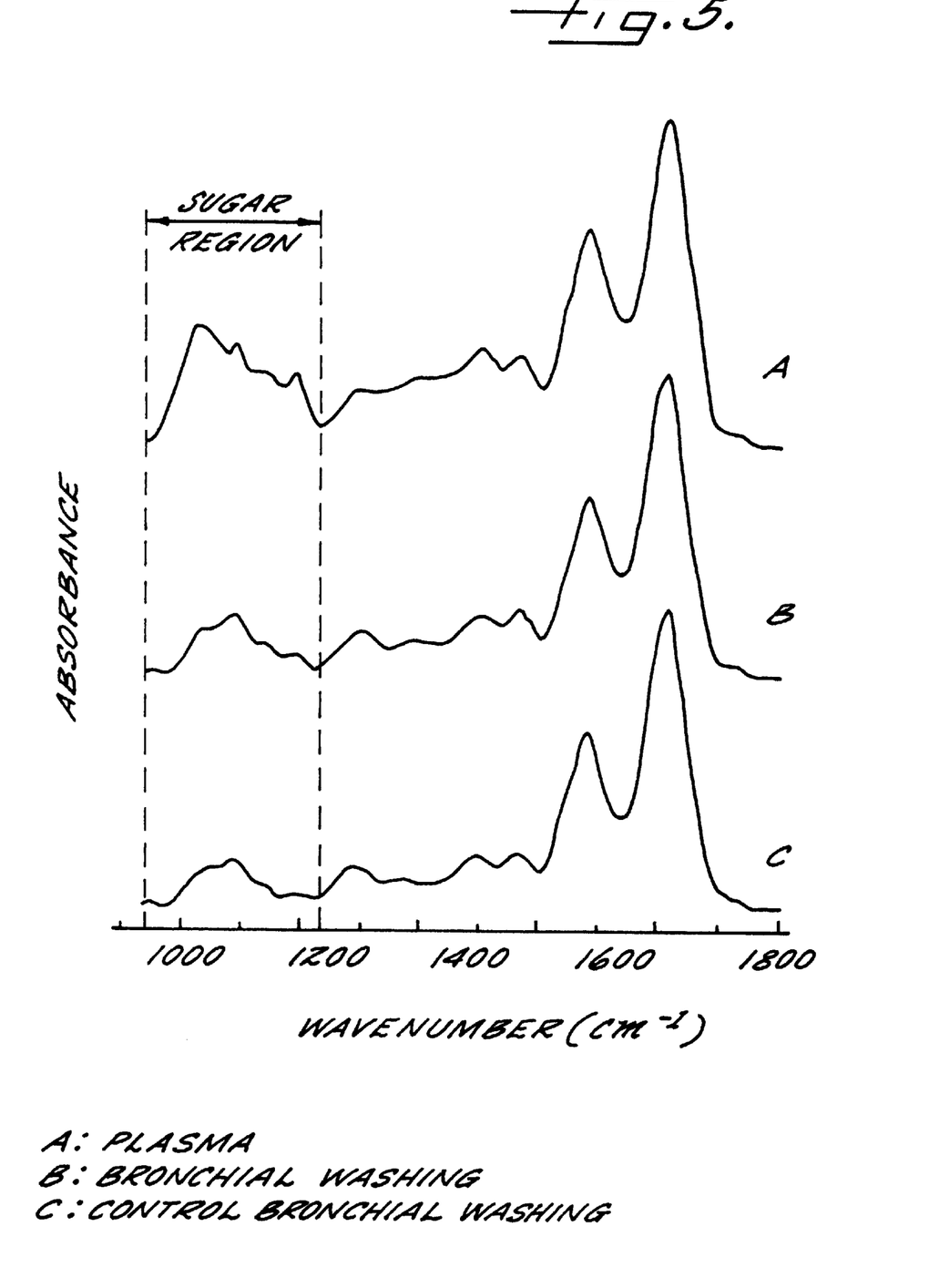
FIGS. 5 and 6 are mid-infrared spectra limited to the range of about 1000 to 1800 $cm^{-1}$.

FIG. 5 demonstrates limited pentastarch infiltration in the bronchial washing of a patient having no apparent lung injury (line B). Despite the plasma loading of pentastarch shown by line A, the sugar region Absorbance of the bronchial washing of line B appears to be substantially identical to the sugar region Absorbance of a bronchial washing obtained from an individual to whom no pentastarch was administered (control, line C). These results are consistent with only the very low molecular weight fraction of the pentastarch infiltrating into the alveolar space of a healthy lung. Interfering absorptions may account for the sugar region Absorbance in line B.

By comparison, the bronchial washing of an ARDS patient shows a dramatic infiltration of pentastarch (FIG. 6, line B, sugar absorption region) that approaches the plasma loading of pentastarch (FIG. 6, line A, sugar absorption region). Also shown in FIG. 6 is the Absorption spectrum of broncho-alveolar-lavage fluid (BALF) from the patient (line C). Comparison of the Absorbance of the sugar region of line C (BALF) with the Absorbance of the sugar region of line B (bronchial washing), confirms the usefulness of a bronchial washing in the methodology of the present invention.

The alveolar macromolecular concentration depends upon the level of circulating macromolecule as well as the alveolo-capillary permeability. Therefore, it is useful to correlate the exogenous marker concentration in bronchial washings or BALF (as determined, for instance, by integrating the sugar region area) with the circulating exogenous marker concentration. To this end, the bronchial fluid/plasma ratio of the marker may be advantageously calculated.

Figure 7:
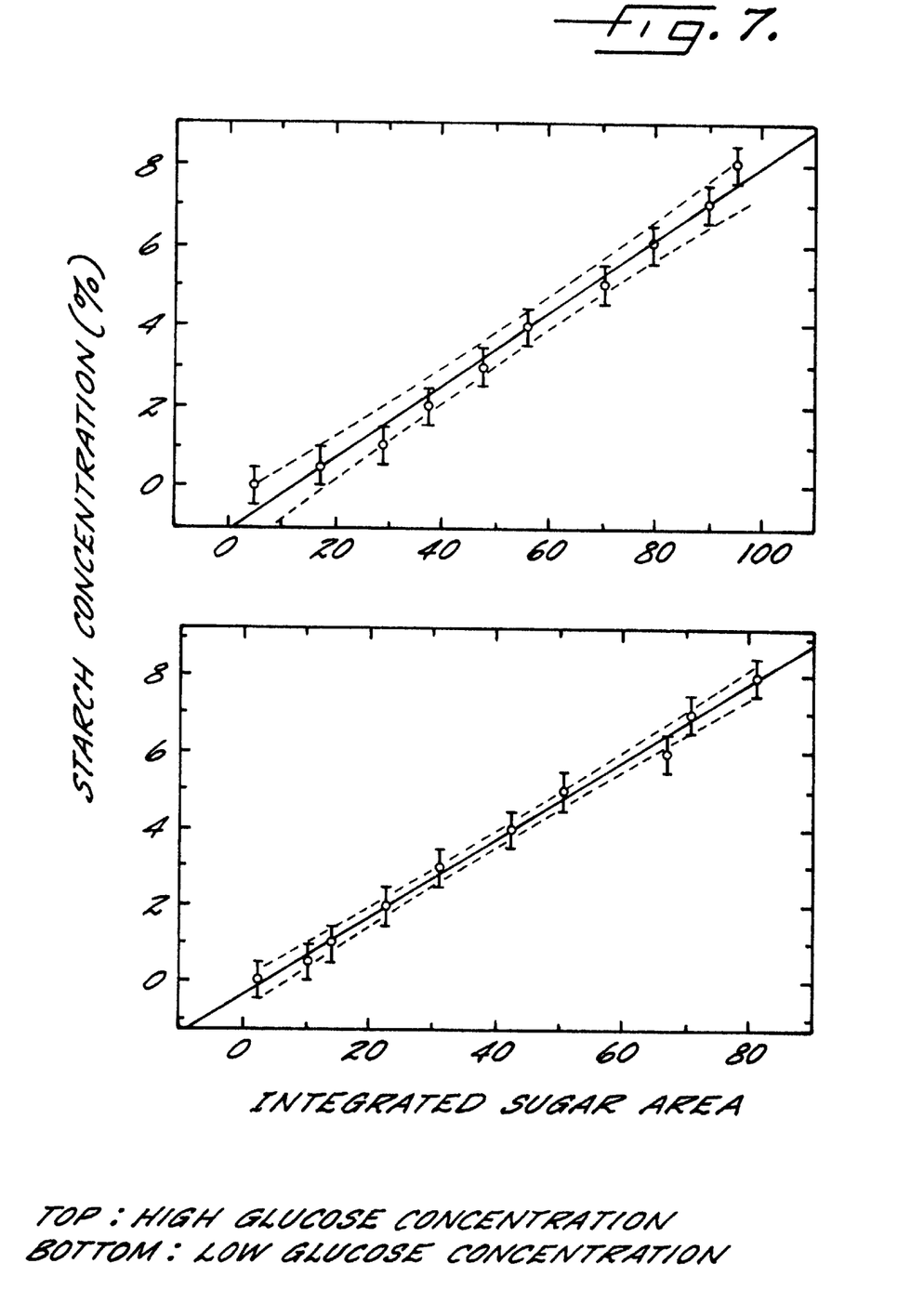
FIG. 7 consists of calibration curves relating to glucose interference.

Although an intense and distinct pattern is observable in the sugar region between 980 to 1190 $cm^{-1}$ for exogenous macromolecules containing sugar moieties and for the hydrolysates, endogenous constituents may interfere. In plasma, potential major interferents are glucose and glycosylated proteins. Using the integrated 980 to 1190 $cm^{-1}$ band area, a calibration curve for starch in plasma over the clinically relevant range of 0.5 to 10% pentastarch is presented in the lower graph of FIG. 7. The calibration has a linear correlation coefficient $R^2=0.9948$ with $p=1.985\times10^{-10}$ significance value. Within this clinically relevant range, FIG. 7 compares glucose interference resulting from a high glucose concentration (150 mg/dL) and from a low glucose concentration (70 mg/dL). Note that the Figure indicates less certainty of the pentastarch concentration, in the case of the high glucose concentration. However, the interference can be corrected for by taking into account spectra before the macromolecule is introduced into the patient. In addition, this interference is less of a problem in the near IR.

The following Example illustrates the present invention. In the Example, bronchial fluid samples are obtained, and samples including blood and urine samples, are prepared for mid-infrared spectroscopic analysis as now described. Bronchial fluid is collected from patients intubated and on positive pressure ventilation, by advancing a suction catheter through the endotracheal tube until a slight resistance is felt. When no fluid comes back spontaneously, a volume of 10 to 20 cc of normal saline is flushed down the catheter. However, when fluid does come back spontaneously, no normal saline is added. After several respiratory cycles, 50 to 75 mm Hg of negative pressure is used for aspiration, and then the catheter is withdrawn. Aspirated fluid is collected in a Lukens trap, the usual yield being about 3 to 4 cc. At or near the time of bronchial fluid collection, blood and urine samples are taken from the patients.

The bronchial fluid, and blood and urine samples are immediately refrigerated and are assayed within 24 hours of collection. In preparation for assay, bronchial fluid samples are homogenized for 2–3 minutes at speed 100 rpm. The homogenized bronchial fluid samples, and blood and urine samples are diluted with distilled water to adjust for the analytical range of the instrument. A volume of 3 microliters of the diluted sample is placed on a 25×2 mm $CaF_2$ window and dried down for 4–5 minutes in a vacuum desiccator to form a film for mid-infrared analysis.

EXAMPLE

Seven patients diagnosed for adult respiratory distress syndrome (ARDS), are evaluated as follows. Each patient is intravenously administered pentastarch (at least 500 ml), and thereafter about one hour or more later, bronchial fluid and blood samples are collected. All patients are intubated and on positive pressure ventilation, and bronchial fluid is collected as earlier described. At or near the time of bronchial fluid collection, blood samples are taken from the patients.

The bronchial fluid and blood samples are immediately refrigerated and are assayed within 24 hours of collection. The samples are prepared for assay as earlier described. A film prepared from each sample is analyzed using mid-infrared spectroscopy: Bio-Rad FTS-40A spectrometer, available from Biorad, Cambridge, Mass., equipped with conventional globar source, KBr beamsplitter and mercury-cadmium-telluride (MCT) detector; spectra recorded at 8 $cm^{-1}$ resolution over the region between 4000 and 900 $cm^{-1}$, consisted of 256 coadded scans.

Figure 8:
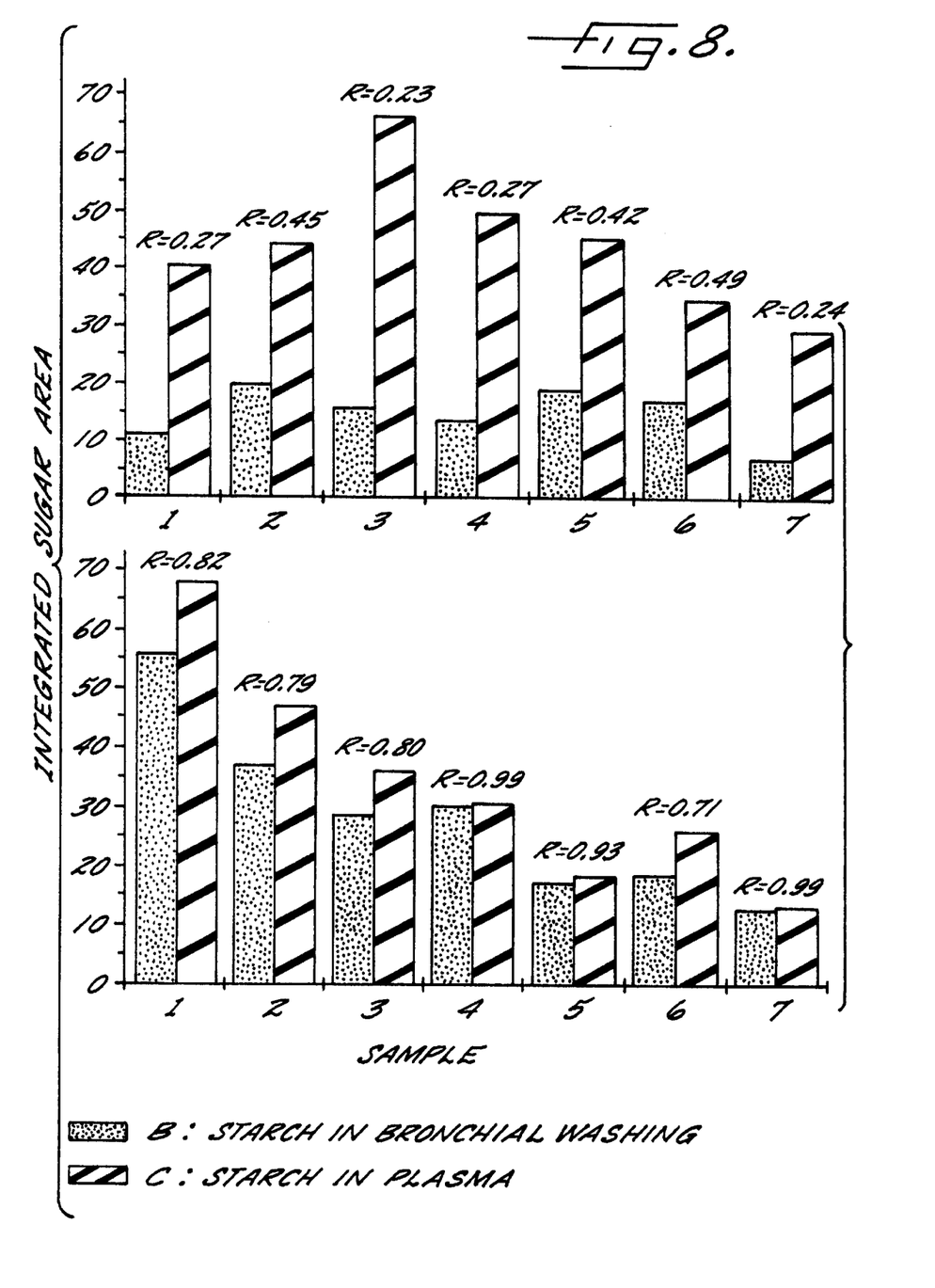
FIG. 8 graphically set forth results of lung permeability analysis in ARDS patients and control patients, obtained using the methodology of the present invention.

In each case, the area of the sugar absorption region (980 to 1190 $cm^{-1}$) of the IR spectrum, is calculated, and thereafter the bronchial fluid/plasma ratio of pentastarch is calculated. The results are shown in FIG. 8, lower graph. As indicated in FIG. 8, the administered dosage of pentastarch varies in the patients. In the ARDS patients studied, the bronchial fluid/plasma ratio of pentastarch is greater than 0.7. As may be understood, clinical progression of lung injury appears to correlate with the ratio, with a relatively higher ratio indicating relatively greater disease progression.

COMPARATIVE EXAMPLE

Seven patients having no clinical evidence of ARDS are used as controls, and are evaluated according to the methodology of the Example. The results are shown in FIG. 8, upper graph. As indicated in the Figure, the administered dosage of pentastarch also varies in these patients. In these patients, the bronchial fluid/plasma ratio of pentastarch is less than 0.5. Low ratios may be the result of interfering absorption, without pentastarch in the bronchial fluid.

The results of the Example and Comparative Example demonstrate the usefulness of the methodology of the present invention, in distinguishing between clinical ARDS and control, even without correcting for interfering absorption. Bronchial fluid samples were corrected for dilution by normalizing against the amide peak.

Figure 9:
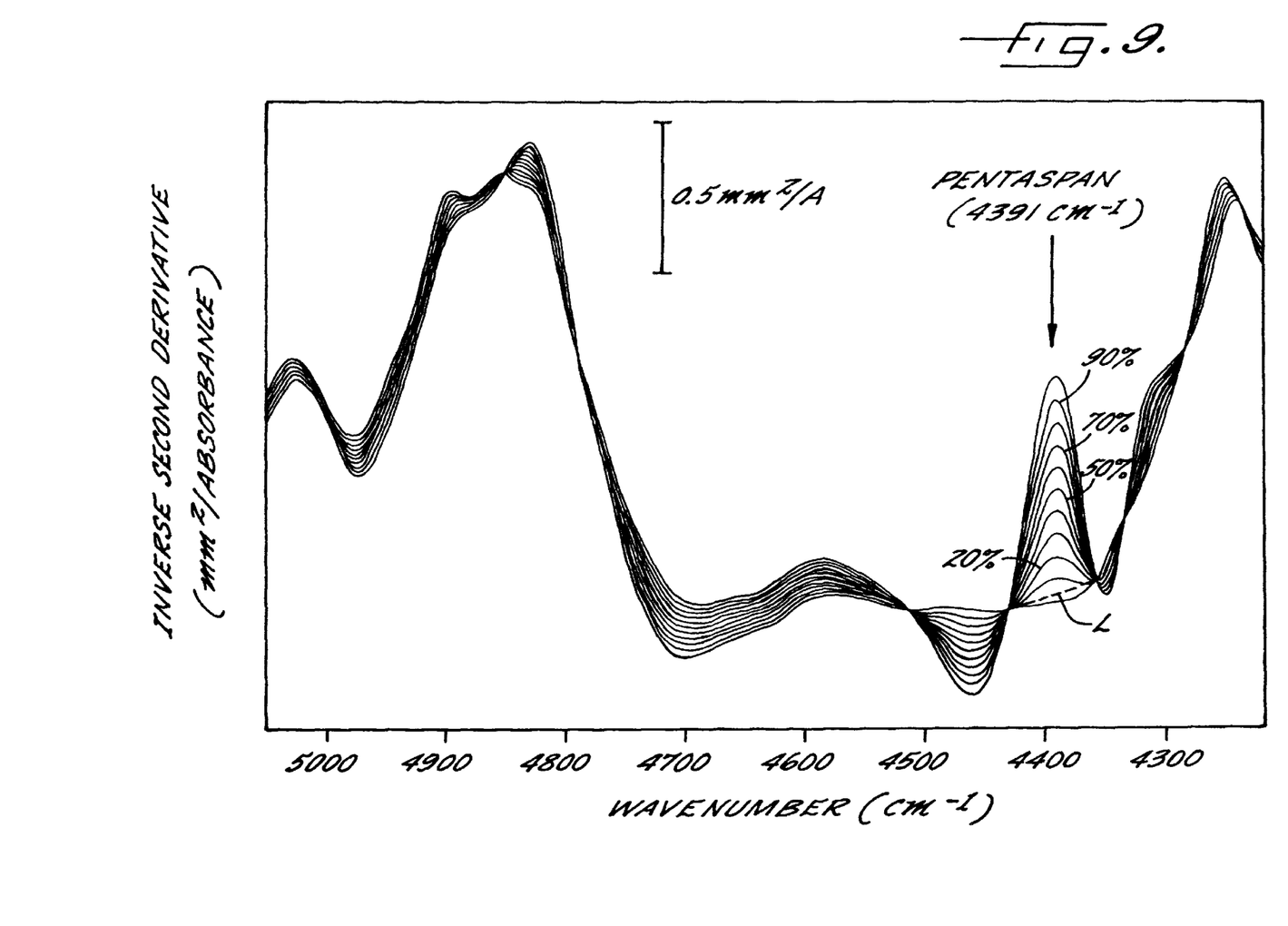
FIG. 9 graphically shows applicability of near-IR spectroscopic analysis to the methodology of the present invention.

Beneficially, in near-infrared spectroscopy, liquid samples may be used, and the liquid samples may be directly analyzed using transmission or reflection spectra. Reflection spectra will typically be preferred. Thus, sample preparation as earlier described, is not necessary. FIG. 9 shows the applicability of near-infrared spectroscopy to the present invention.

The data of FIG. 9 are obtained as follows using a second derivative approach. Bronchial washings are collected and to nine portions of the washings, pentastarch is added to produce final concentrations of 10%, 20%, 30%, 40%, 50%, 60%, 70%, 80% and 90% pentastarch. A starch-free bronchial washing, the 10% to 90% pentastarch-containing washings, and a 100% pentastarch solution are thereafter analyzed in a 5 mm pathlength quartz transmission cell using an NIR Systems (Silver Springs, Md.) spectrophotometer. The second derivatives of the original spectra are then determined and converted to the inverse of the second derivatives. Thereafter to obtain FIG. 9, the inverse of the second derivatives is plotted against wavenumber.

Examination of the family of curves so obtained, shows that suitable data can be obtained using near infrared spectroscopy based upon concentration changes of a useful exogenous macromolecule in accordance with the present invention, and in particular in the about 4350 to 4500 $cm^{-1}$ region for concentration changes of pentastarch. Members of the family of curves are labelled in the about 4350 to 4450 $cm^{-1}$ region, to indicate the percentage of pentastarch.

Figure 10:
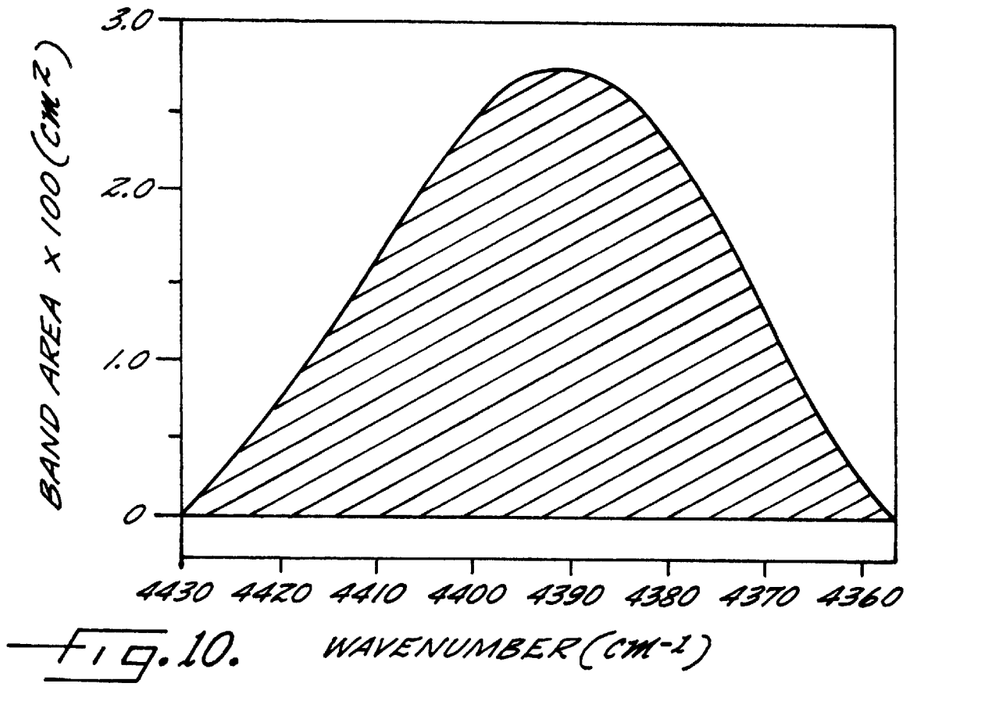
FIG. 10 graphically shows further details relative to the 90% pentastarch concentration sample used in FIG. 9.

In FIG. 10, the total area encompassed by the curve labelled 90% in FIG. 9 (the baseline for defining the total area being a dashed line L in FIG. 9) is plotted against wavenumber. As may be seen in FIG. 10, the optimal wavenumber is about 4390 $cm^{-1}$, and a useful wavenumber range is more precisely from about 4360 to 4430 $cm^{-1}$.

Figure 10A:
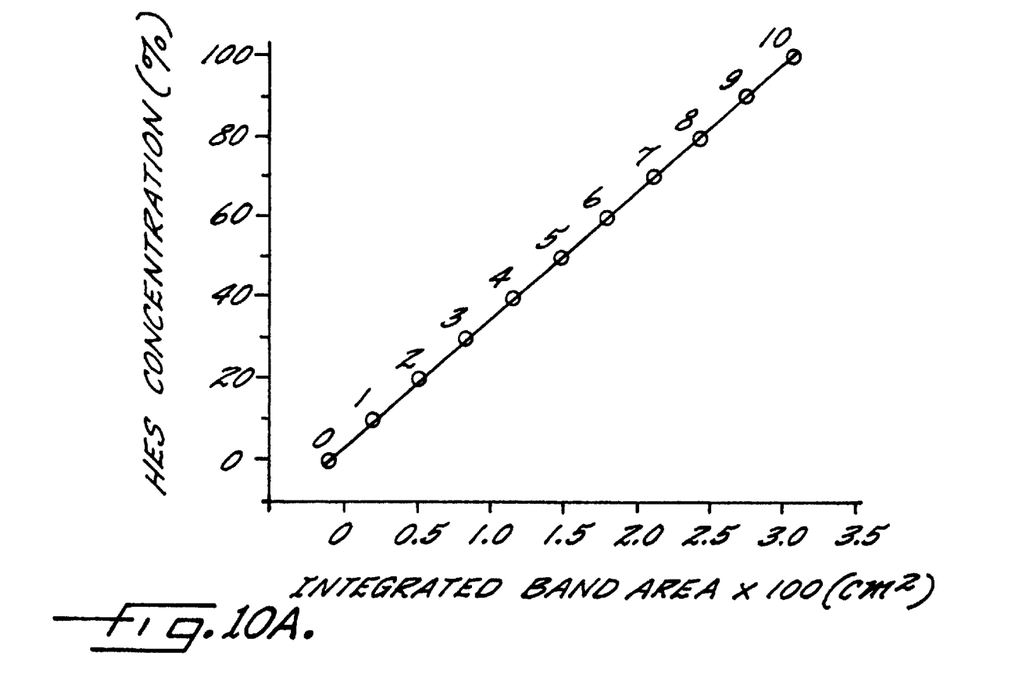
FIG. 10A is a calibration curve.

In FIG. 10A, data obtained for FIG. 9 is used for plotting pentastarch (indicated "HES" in FIG. 10A) concentration (0 to 100%) against integrated band area of the respective concentration. A satisfactory calibration curve is shown. Conversely, changes in albumin concentration do not affect the spectra in this near IR region. Therefore, near IR spectroscopy is useful in the present invention.

The average molecular weight of the exogenous macromolecule in plasma may be obtained by, for instance, osmotic measurements through a semipermeable membrane. This result advantageously indicates the relevance of the bronchial fluid/plasma ratio in assessing permeability. Thus, infiltration in bronchial washings, when the average molecular weight of the macromolecule is large, represents an increased permeability. Conversely, infiltration when the average molecular weight of the macromolecule is small, may be compatible with a normal permeability.

Having described the invention in detail and by reference to preferred embodiments, it will be apparent that modifications and variations are possible.

We claim:

1. A spectrophotometric analytical method of analysis without the use of a radioactive- or dye-labeled tracer comprising administering to a patient an appropriate dosage of a suitable exogenous polydispersed macromolecule without a radioactive or dye label but having a distinctive spectroscopic infrared signature, and analyzing bronchial fluid of said patient by infrared spectrophotometric analysis for said exogenous macromolecule.

2. The method of claim 1, wherein said analysis is carried out using near-IR spectroscopy.

3. The method of claim 1, wherein said analysis utilizes near-IR spectroscopy in the range of about 4350 to 4500 $cm^{-1}$.

4. The method of claim 1, wherein said analysis utilizes mid-IR spectroscopy in the range of about 900 to 1200 $cm^{-1}$.

5. The method of claim 1, further comprising determining the concentration of said exogenous macromolecule in said bronchial fluid.

6. The method of claim 1, further comprising analyzing urine of said patient by infrared spectrophotometric analysis for said exogenous macromolecule.

7. The method of claim 1, wherein said exogenous macromolecule comprises a pyranosyl moiety.

8. The method of claim 1, wherein said exogenous macromolecule is a polydispersed colloid.

9. The method of claim 1, wherein said exogenous macromolecule is pentastarch.

10. The method of claim 1, further comprising analyzing plasma of said patient by infrared spectrophotometric analysis for said exogenous macromolecule.

11. The method of claim 10, further comprising determining a bronchial fluid/plasma ratio of said exogenous macromolecule.

* * * * *